United States Patent [19]

Hibino et al.

[11] 3,932,400

[45] Jan. 13, 1976

[54] THIAZOLE DERIVATIVES

[75] Inventors: Toshihiko Hibino, Takarazuka; Yoshio Suzuki, Itami; Shigeru Okano, Kawani; Yoichi Hara, Toyonaka; Etsuro Sato, Takarazuka, all of Japan

[73] Assignee: Sumitomo Chemical Company, Limited, Japan

[22] Filed: Aug. 16, 1973

[21] Appl. No.: 389,517

[30] Foreign Application Priority Data

Aug. 17, 1972 Japan.................................. 47-82574
Apr. 5, 1973 Japan.................................. 48-39354

[52] U.S. Cl....................... 260/247.1 M; 260/243 B; 260/250 BN; 260/256.5 R; 260/287 F; 260/287 CE; 260/288 CE; 260/293.68; 260/294.8 D; 260/302 H; 260/302 S; 260/293.57; 424/246; 424/248; 424/250; 424/251; 424/258; 424/263; 424/267; 424/270
[51] Int. Cl.²......................................... C07D 277/36
[58] Field of Search..... 260/302 S, 302 H, 247.1 M, 260/293.68

[56] References Cited
UNITED STATES PATENTS

| 2,221,147 | 11/1940 | Mathes............................ | 260/302 S |
| 3,158,623 | 11/1964 | Von Esch et al............... | 260/302 H |
| 3,228,952 | 1/1966 | Reifschneider.................. | 260/302 S |

FOREIGN PATENTS OR APPLICATIONS

| 599,475 | 6/1960 | Canada............................ | 260/302 S |

OTHER PUBLICATIONS

Wagner et al., Synthetic Organic Chemistry, N.Y., John Wiley & Sons, 1953, pp. 787–788.

*Primary Examiner*—Richard J. Gallagher
*Attorney, Agent, or Firm*—Wenderoth, Lind & Ponack

[57] ABSTRACT

This invention relates to thiazole derivatives of the formula (I):

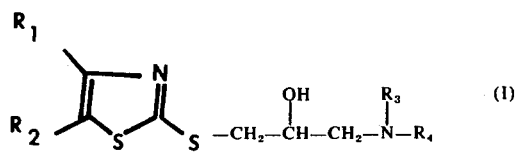

wherein $R_1$ and $R_2$ are each hydrogen, lower alkyl, cycloalkyl, optionally substituted aryl or optionally substituted heteroaromatic rings containing oxygen, sulfur, nitrogen or combinations thereof, and $R_3$ and $R_4$ are each hydrogen or lower alkyl and salts thereof. The thiazole derivatives of the formula (I) have excellent pharmacological properties such as β-adrenergic receptor blocking effects and are valuable compounds exerting preventive or therapeutic effects on heart diseases, for example, arrhythmia, coronary heart disease, etc.

10 Claims, No Drawings

THIAZOLE DERIVATIVES

This invention relates to novel thiazole derivatives of the formula (I);

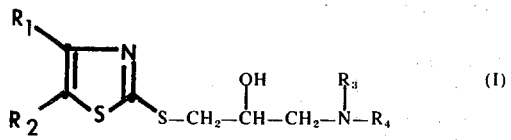

wherein $R_1$ and $R_2$ are each hydrogen, lower alkyl, cycloalkyl, optionally substituted aryl or optionally substituted heteroaromatic ring containing oxygen, sulfur, nitrogen or these combination, and $R_3$ and $R_4$ are each hydrogen or lower alkyl, and salts thereof and to the production thereof.

In the above significances, "lower alkyl" includes $C_1 - C_4$ alkyl (for example, methyl, ethyl, n-propyl, iso-propyl, n-butyl, iso-butyl, sec-butyl, t-butyl), and methyl, ethyl, iso-propyl, and t-butyl are preferable.

The term "optionally substituted aryl" means to include phenyl, substituted phenyl, naphthyl and substituted naphthyl and, as the substituent of the substituted phenyl and naphthyl, there may be mentioned $C_1 - C_4$ alkyl (for example, methyl, ethyl, n-propyl, iso-propyl, n-butyl, iso-butyl, sec-butyl, t-butyl), $C_1 - C_4$ alkoxy (for example, methoxy, ethoxy, n-propoxy, iso-propoxy, n-butoxy, iso-butoxy, t-butoxy), hydroxyl, $C_3 - C_5$ alkenyl (for example, propenyl, butenyl, hexenyl), $C_3 - C_5$ alkenyloxy (for example, propenyloxy, butenyloxy,), halogeno (for example, iodo, chloro, bromo, fluoro), cyano, amino, nitro, aryloxy (for example, phenoxy, naphthoxy) and acylamino (for example, acetoamido, propionamido, benzamido).

The term "cycloalkyl" means to include $C_3 - C_6$ cycloalkyl, among which cyclohexyl is preferable.

The term "optionally substituted heteroaromatic ring" includes 5 and 6 membered ring containing oxygen, sulfur, nitrogen or these combination and rings formed by the condensation thereof with benzene ring, preferable ones including furyl, thienyl, pyrrolyl, thiazolyl, iso-thiazolyl, imidazolyl, pyrazolyl, oxazolyl, isoxazolyl, pyridyl, pyrimidinyl, pyrazinyl, benzothienyl, benzoimidazolyl, indolyl and quinolyl. Among them, furyl, thienyl, thiazolyl, pyrrolyl, pyridyl are most preferable. As the substituent of these hetero aromatic ring, there may be exemplified lower alkyl, lower alkoxy, halogen, amino, nitro, cyano, phenyl, acylamino, group of the formula

(wherein Y is hydroxy, lower alkyl, lower alkoxy or lower alkenyloxy) and group of the formula

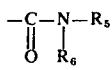

(wherein $R_5$ and $R_6$ are each hydrogen, amino, lower alkyl, cycloalkyl, optionally substituted aryl and, when taken together with adjacent nitrogen, may forms a hetero cyclic group). In the above the term "acylamino" may include $C_2 - C_8$ acylamino, (for example, acetamido, propionamido, benzamido), and the term "lower alkenyloxy" includes $C_3 - C_5$ alkenyloxy (for example, propenyloxy, butenyloxy, hexenyloxy), and the term "cycloalkyl" includes $C_3 - C_6$ cycloalkyl wherein cyclopropyl, cyclopentyl and cyclohexyl are preferable, and the term "heterocyclic group" includes 5 and 6 membered heterocyclic group, in which morpholinyl, pyrrolidinyl, piperidyl and thiomorpholinyl are preferable. The other terms "lower alkyl", "lower alkoxy", "halogen" and "optionally substituted aryl" are the same meanings as mentioned above.

A principal object of the present invention is to provide novel thiazole derivatives of the formula (I).

Another object of the present invention is to provide a process for producing novel thiazole derivatives of the formula (I).

Still another object is to provide a pharmaceutical composition containing an effective amount of at least one thiazole derivative of the formula (I) and pharmaceutically acceptable carrier.

Other objects will be apparent from the following description.

The thiazole derivatives of the formula (I) have excellent pharmacological properties such as $\beta$-adrenergic receptor blocking effect and are valuable compounds exerting preventive or therapeutic effect on a heart disease, for example, arrhythmia, coronary heart disease, etc.

In order to show such properties, $\beta$-adrenergic receptor blocking activity and acute toxicity of thiazole derivatives of the formula (I) are compared with propranolol and practolol which are commercially available compounds and are known as one of the most effective compounds in the field of this invention. As will be appreviated from the following Tables, thiazole derivatives of the formula (I) have stronger or same $\beta$-adrenergic receptor blocking activity but less toxicity as compared with propranolol and practolol.

Table 1

| Compound | $\beta$-adrenergic receptor blocking activity in open chest dog (propranolol = 1) | | |
|---|---|---|---|
| | DPC | DPI | DDE |
| compd. of Example 23 | 2 | 1.5 | 4 |
| compd. of Example 37 | 15 | 15 | 8 |
| compd. of Example 35 | 2 | 3 | 0.8 |
| Propranolol | 1 | 1 | 1 |
| Practolol | 0.5 | 0.7 | 0.08 |

Note: A determination of $\beta$-adrenergic receptor blocking activity of test compounds in open chest dog was as follows. Thus dogs were anesthetized with pentbarbital sodium (administrated 30 – 40 mg./kg. intravenously). Heart rate, myocardial contractile force and blood pressure were recorded with NIHON KODEN RM-150 polygraph. A depressive effect of test compounds on positive chronotropic (DPC), positive inotropic (DPI) and depressor effect (DDE) induced by isoproternol, which was injected intraveneously at a quarter interval, was determined.

Table 2

| Compound | Acute toxicity LD$_{50}$ (mg./kg.) |
|---|---|
| compd. of Example 23 | 46 |
| compd. of Example 37 | 86 |
| compd. of Example 35 | 60 |
| Propranolol | 23 |

Note: For the determination of the intravenous LD$_{50}$, 10 male mice were used and the method of up and down was used for calculation of the LD$_{50}$.

According to the present invention, the thiazole derivatives of the formula (I)

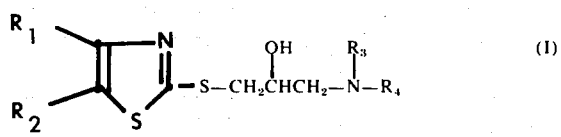

(I)

wherein $R_1$, $R_2$, $R_3$ and $R_4$ have the same meanings as defined before, are prepared by reating an aminoalcohol of the formula (II)

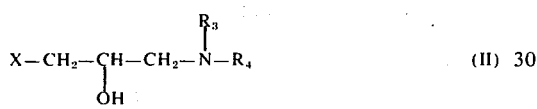

(II)

wherein $R_3$ and $R_4$ have the same meanings as defined before and X is halogen, with a 2-mercaptothiazole derivative of the formula (III)

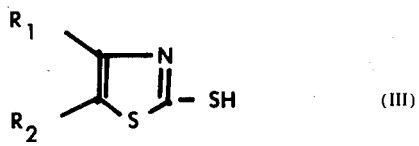

(III)

wherein $R_1$ and $R_2$ have the same meanings as defined before.

More particularly, the thiazole derivatives of the formula (I) are prepared by reacting a 2-mercaptothiazole derivative of the formula (III) in the presence of water, organic solvent (for example, alcohol, dioxane) or water-organic solvent (for example, water-alcohol, water-dioxane) with equal moles of the aminoalcohol of the formula (II).

In this case, the reaction is preferablly carried out in the presence of organic or inorganic base such as sodium hydroxide, potassium hydroxide, sodium carbonate, potassium carbonate, pyridine or tertiary amine.

In order to avoid oxidation and polymerization of aminoalcohol (II) this reaction is preferably carried out under nitrogen gas atmosphere at a temperature below 25°C.

Alternatively, the present thiazole derivatives (I) may quantitatively be prepared by treating a 2-mercaptothiazole derivative (III) with an inorganic base such as potassium hydroxide, sodium hydroxide, potassium carbonate or sodium carbonate on aqueous alcohol to form form the salt and then reacting the salt with an aminoalcohol (II), and this method is particularly advantageous for commercially producing the thiazole derivatives (I), thus obtained thiazole derivatives and salts thereof can be isolated and refined by a conventional procedure such as extraction, recrystallization, reprecipitation, column chromatography or treatment with carbon powder, and can be converted to the pharmaceutically acceptable salts with inorganic or organic acid (for example, hydrochloric acid, sulfuric acid, phosphoric acid, tartaric acid) according to a conventional procedure.

2-mercaptothiazole derivatives (III) can be prepared according to a conventional method. One example is illustrated below.

(Journal of The Organic Chemistry; 6, 764 (1941), Journal of The Chemical Society; 1945, 925, U.S.P. 2,186,421)

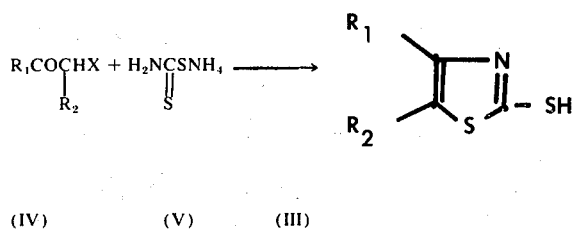

(IV)     (V)     (III)

In this reaction, mercaptothiazole derivatives (III) are prepared by reacting the compound (IV) with equal moles of the compound (V). When the compound (IV) is unstable in free-amine form, this reaction is preferably carried out by reacting the salt of the compound (IV) (for example, hydrochloric acid salt) with two moles of the compound (V).

Thiazole derivatives (I) and salts thereof may be brought into a suitable form such as tablet, powder, solution, capsule, injection or emulsion for administration according to the conventional method and may be administered orally or parenterally.

The usual dosage of thiazole derivatives (I) of the present invention is within a range of 1 mg./day to 1000 mg./day.

In order to illustrate the invention in details, the following Examples are given but not by way of limitation.

EXAMPLE 1

2-(3'-t-butylamino-2'-hydroxypropylthio)-4-phenyl thiazole hydrochloride.

To a solution of 2 mercapto-4-phenyl thiazole, 5.78 g. in 100 ml. of 2.2 % aqueous sodium hydroxide solution, 1-chloro-3-t-butylaminopropanol, 7.85 g. in 150 ml. of methanol was added dropwise.

The reaction solution added with 10 % aqueous sodium hydroxide solution, was extracted with chloroform. The extract was washed with water, dried and evaporated to have a pale yellowish oil, which was purified by chromatography on alumina column in chloroform.

The oil was treated with 5 % alcoholic hydrogen chloride solution, and a precipitate was recrystallized from acetone-methanol to yield 2-(3'-t-butylamino-2'-hydroxypropylthio)-4-phenyl thiazole hydrochloride; white solid, m.p. 169° – 174°C.

$C_{16}H_{22}N_2OS_2 \cdot 2HCl$

Anal. Calcd. for
C; 48.48, H; 6.06, N; 7.07, S; 16.16,
Cl; 18.43 (%)
Found
C; 48.34, H; 6.15, N; 6.83, S; 15.11, Cl; 17.00 (%)

According to Example 1, the following compounds were synthesized.

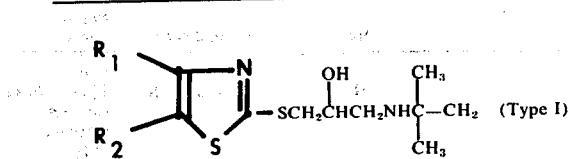

| Example No. | $R_1$ | $R_2$ | Isolated form | Physical const. |
|---|---|---|---|---|
| 2 | $CH_3$ | phenyl | hydrochloride | m.p. 205 – 206°C. (acetone-methanol) |
| 3 | naphthyl | H | hydrochloride | m.p. 204 – 205°C. (acetone) |
| 4 | $CH_3$ | H | hydrochloride | m.p. 210 – 214°C. (acetone) |
| 5 | phenyl | $CH_3$-phenyl | free base | m.p. 101°C. (benzene-light petroleum) |
| 6 | F-phenyl | H | hydrochloride | m.p. 180–183°C. (acetone-methanol) |
| 7 | $CH_3O$-phenyl | H | free base | $n_d^{28}$ 1.5936 |
| 8 | $CH_3$-phenyl | H | hydrochloride | m.p. 158 – 161°C. (acetone-methanol) |
| 9 | naphthyl | H | free base | $n_d^{25}$ 1.6162 |
| 10 | methylfuryl | H | hydrochloride | m.p. 150 – 153°C. (acetone-ethanol) |
| 11 | Br-phenyl | H | hydrochloride | m.p. 178 – 180°C. (acetone-methanol) |
| 12 | OH-phenyl | H | free base | $n_d^{29}$ 1.5968 |
| 13 | NC-phenyl | H | hydrochloride | m.p. 138 – 143°C. (acetone-ethanol) |
| 14 | $OCH_2CH-CH_2$-phenyl | H | hydrochloride | m.p. 169 – 171°C. (acetone-methanol) |
| 15 | dimethylfuryl | H | free base | $n_d^{24.5}$ 1.5745 |

-continued

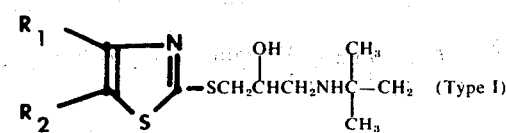

| Example No. | R₁ | R₂ | Isolated form | Physical const. |
|---|---|---|---|---|
| 16 | cyclohexenyl | H | hydrochloride | m.p. 171 – 174°C. (acetone-methanol) |
| 17 | 4,5,6,7-tetrahydrobenzothienyl | H | hydrochloride | m.p. 176 – 177°C. (acetone-methanol) |
| 18 | 1-methylpyrrolyl | H | hydrochloride | m.p. 140 – 143°C. (acetone-ethanol) |
| 19 | phenyl | H | free base | $n_d^{26}$ 1.5979 |
| 20 | 2,4-dimethylthiazolyl | H | hydrochloride | m.p. 278 – 279°C. (methanol-water) |
| 21 | benzothiazolyl | H | free base | m.p. 146 – 147°C. (benzene-light petroleum) |

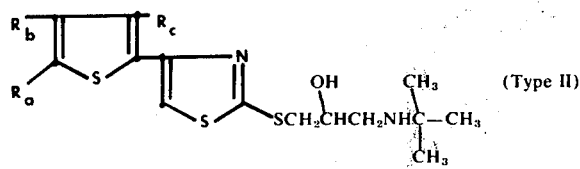

| Example No. | $R_a$ | $R_b$ | $R_c$ | Isolated form | Physical const. |
|---|---|---|---|---|---|
| 23 | H | H | H | picrate | m.p. 153 – 154°C. ($CHCl_3$) |
| 24 | $CH_3$ | H | H | hydrochloride | m.p. 123 – 124°C. (acetone) |
| 25 | H | H | $CH_3$ | free base | $n_d^{25}$ 1.6030 |
| 26 | Br | $CH_3$ | H | hydrochloride | m.p. 176 – 177°C. (acetone-methanol) |
| 27 | $CH_3$ | $CH_3$ | H | hydrochloride | m.p. 229 – 230°C. (acetone-methanol) |
| 28 | $CH_3CH_2-$ | H | H | hydrochloride | m.p. 148 – 149°C. (acetone- |

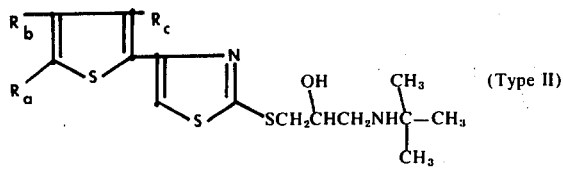

(Type II)

| Example No. | $R_a$ | $R_b$ | $R_c$ | Isolated form | Physical const. |
|---|---|---|---|---|---|
| 29 | CH₃CHCH₂—<br>\|<br>CH₃ | H | H | hydrochloride | (methanol)<br>m.p.<br>145 – 146°C. |
| 30 | (phenyl) | H | H | free base | (chloroform-methanol)<br>$n_d^{25}$ 1.5966 |
| 31 | Br | H | H | hydrochloride | m.p.<br>173 – 173.5°C.<br>(acetone-methanol) |
| 32 | I | H | H | hydrochloride | m.p.<br>165 – 166°C.<br>(acetone-methanol) |
| 33 | CN | H | H | free base | $n_d^{21.5}$ 1.6009 |
| 34 | H | H | CN | hydrochloride | m.p.<br>160 – 161°C.<br>(acetone-methanol) |
| 35 | NO₂ | H | H | hydrochloride | m.p.<br>236 – 237°C.<br>(acetone-methanol) |
| 36 | H | NO₂ | H | hydrochloride | m.p.<br>174 – 175°C.<br>(acetone-methanol) |

EXAMPLE 37

2-(3'-t-butylamino-2'-hydroxypropylthio)-4-(5'-carbamoyl-2'-thienyl)thiazole.

To a solution of 2-mercapto-4-(5'-carbamoyl-2'-thienyl)thiazole, 3.2 g. in 20 ml. of 0.3% aqueous sodium hydroxide solution, 1-chloro-3-t-butylaminopropanol, 12.64 g. in 20 ml. of methanol was added, while the temperature was maintained at 20°C.

The reaction solution was stirred at room temperature for 4 hours, and then condensed to a half volume in vacuo.

The residual solution, added with 100 ml. of water, was extracted with chloroform.

The chloroform extract was washed with water, dried over anhydrous magnesium sulfate and evaporated in vacuo to give a residue, 4.8 g., which was recrystallized from chloroform-light petroleum to yield 2-(3'-t-butylamino-2'-hydroxypropylthio)-4-(5'-carbamoyl-2'-thienyl)thiazole; needles, m.p. 148° – 149°C.

$C_{15}H_{21}O_2N_3S_3$
Anal. Calcd. for
  C; 48.52,    H; 5.66,    N; 11.32,    S; 25.88   (%)
Found
  C; 48.31,    H; 5.42,    N; 11.15,    S; 25   (%)

According to Example 37, the following compounds were synthesized.

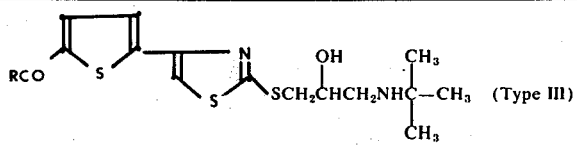

(Type III)

| Example No. | R | Isolated form | Physical const. |
|---|---|---|---|
| 38 | CH₃NH | hydrochloride | m.p. 142 – 144°C.<br>(acetone-methanol) |
| 39 | CH₃(CH₂)₃NH | hydrochloride | m.p. 106 – 108°C.<br>(acetone-methanol) |

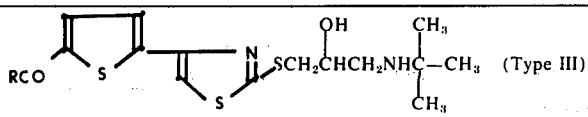
(Type III)

| Example No. | R | Isolated form | Physical const. |
|---|---|---|---|
| 40 | piperidino | hydrochloride | m.p. 163 – 165°C. (acetone-methanol) |
| 41 | pyrrolidino | hydrochloride | m.p. 165 – 166°C. (acetone-methanol) |
| 42 | morpholino | hydrochloride | m.p. 178 – 179°C. (acetone-methanol) |
| 43 | $H_2NNH-$ | hydrochloride | m.p. 202 – 207°C. (acetone-methanol) |
| 44 | $(CH_3CH_2)_2N-$ | hydrochloride | m.p. 152 – 153°C. (acetone-methanol) |
| 45 | cyclohexyl-NH– | free base | m.p. 140 – 141°C. (light petroleum-benzene) |
| 46 | $(CH_3)_3C-O-$ | hydrochloride | m.p. 251 – 252°C. (acetone-methanol) |
| 47 | $CH_3-$ | free base | $n_d^{25}$ 1.6032 |

EXAMPLE 48

2-(3'-t-butylamino-2'-hydroxypropylthio)-4-(5'-ethoxycarbonyl-2'-thienyl)thiazole hydrochloride.

A solution of 2-(3'-t-butylamino-2'-hydroxypropylthio)-4-(5'-t-butoxycarbonyl-2'-thienyl)thiazole, 1.0 g. in 50 ml. of 3 % $H_2SO_4$ ethanolic solution was refluxed for 3.5 hours.

After cooling, the solution was neutralized with sodiumbicarbonate (solid), filtered and dried up in vacuo to a residue, which was extracted with chloroform. The chloroform extract was washed with satd. $NaHCO_3$ aqueous solution, dried and evaporated to a residue, which was converted to its hydrochloride salt followed recrystallization from acetone to yield 0.3 g. of 2-(3'-t-butylamino-2'-hydroxypropylthio)-4-(5'-ethoxycarbonyl-2'-thienyl)thiazole hydrochloride, m.p. 118° – 119°C.

$C_{17}H_{25}O_3N_2S_3Cl$

Anal. Calcd. for
C; 46.73, H; 5.72, N; 6.41, S; 21.99, Cl; 8.13 (%)

ound
C; 46.73, H; 5.61, N; 6.46, S; 21.78, Cl; 8.42 (%)

The following two esters were synthesized according to Example 48.

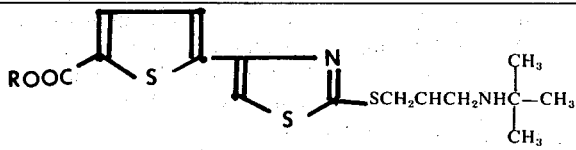
(Type IV)

| Example No. | R | Isolated form | Physical const. |
|---|---|---|---|
| 49 | $CH_3$ | hydrochloride | m.p. 124 – 126°C. (acetone) |
| 50 | $CH_2CH=CH_2-$ | hydrochloride | m.p. 135 – 136°C. (acetone) |

EXAMPLE 51

2-(3'-t-butylamino-2-hydroxypropylthio)-4-(5'-carboxyl 2'-thienyl)thiazole hydrochloride.

A solution of 2-(3'-t-butylamino-2'-hydroxypropylthio)-4-(5'-t-butoxycarbonyl-2'-thienyl)thiazole hydrochloride, 0.34 g. in 20 ml. of 5 % methanolic hydrochloride solution was stood at room temperature for 30 minutes and then dried up in vacuo.

Recrystallization of a residue from acetone yielded 2-(3'-t-butylamino-2'-hydroxypropylthio)-4-(5'-carboxy-2′-thienyl)thiazole hydrochloride; needles, m.p. 251° – 252°C.

| $C_{15}H_{20}O_3N_2S_3 \cdot HCl$ | | | | |
|---|---|---|---|---|
| Anal. Calcd. for | | | | |
| C; 44.06, | H; 5.14, | N; 6.85, | S; 23.50, | Cl; 8.69 |
| Found | | | | |
| C; 43.88, | H; 5.32, | N; 6.90, | S; 22.85, | Cl; 8.43 |

What is claimed is:
1. A novel thiazole derivative of the formula:

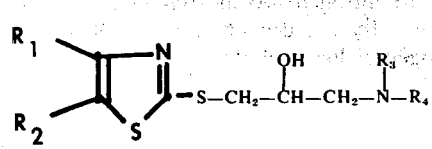

wherein $R_1$ is hydrogen, $C_1$ - $C_4$ alkyl, $C_4$ - $C_6$ cycloalkyl, naphthyl, phenyl, phenyl substituted by a member selected from the group consisting of $C_1$ - $C_4$ alkyl, $C_1$ - $C_4$ alkoxy, hydroxyl, $C_3$ - $C_5$ alkenyl, $C_3$ $C_5$ alkenyloxy, iodo, chloro, bromo, fluoro, cyano, amino, nitro, phenoxy, naphthoxy, acetamido, propionamido and benzamido or naphthyl substituted by a member selected from the group consisting of $C_1$ - $C_4$ alkyl, $C_1$ - $C_4$ alkoxy, hydroxy, fluoro, iodo, chloro or bromo, cyano, amino, nitro, acetamido, propionamido and benzamido, and $R_2$ is hydrogen and $R_3$ and $R_4$ are each hydrogen or $C_1$ - $C_4$ alkyl.

2. A novel thiazole derivative of the formula,

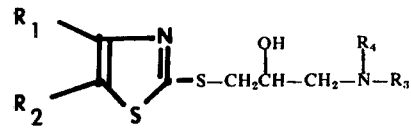

wherein $R_1$ and $R_2$ are hydrogen, methyl, cyclohexyl, naphthyl, phenyl or substituted phenyl having a group selected from the group consisting of methyl, methoxy, allyloxy, hydroxy, fluoro, bromo and cyano, and $R_3$ and $R_4$ are each hydrogen or t-butyl.

3. A novel thiazole derivative of the formula,

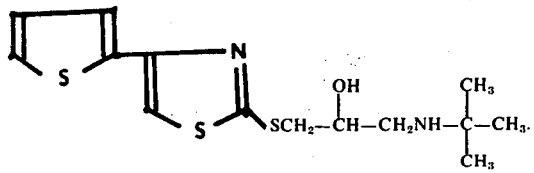

4. A novel thiazole derivative of the formula,

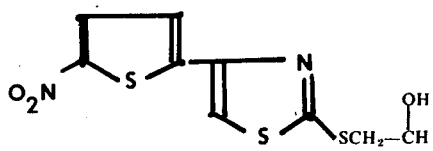

5. A novel thiazole derivative of the formula,

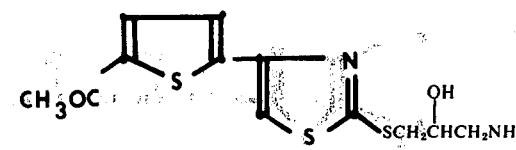

6. A novel thiazole derivative of the formula,

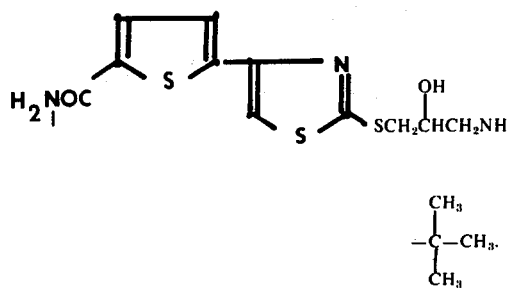

7. A novel thiazole derivative of the formula:

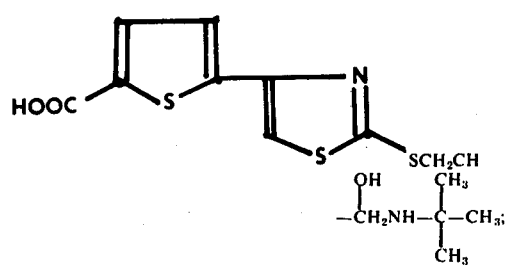

8. A thiazole derivative of the formula:

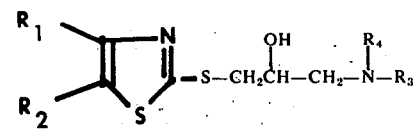

wherein $R_1$ is furyl or $C_1$ - $C_4$ alkylfuryl, $R_2$ is hydrogen and $R_3$ and $R_4$ are each hydrogen or lower alkyl.

9. A thiazole derivative of the formula:

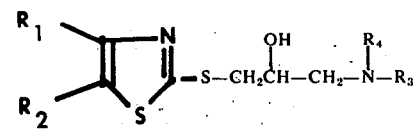

wherein $R_1$ is pyrrolyl or $C_1$ - $C_4$ alkyl pyrrolyl, $R_2$ is hydrogen and $R_3$ and $R_4$ are each hydrogen or $C_1$ - $C_4$ alkyl.

10. A thiazole derivative of the formula

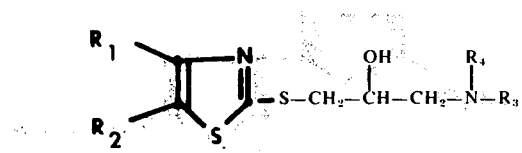

wherein $R_1$ is thienyl or substituted thienyl having one or more groups selected from the group consisting of $C_1 - C_4$ alkyl, phenyl, bromo, iodo, nitro,

wherein Y is $C_1 - C_4$ alkoxy, methyl or propenyloxy or

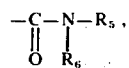

wherein $R_5$ and $R_6$ are each hydrogen, $C_1 - C_4$ alkyl, amino or cyclohexyl and when taken together with adjacent nitrogen are morpholinyl, piperidyl or pyrrolidinyl, $R_2$ is hydrogen and $R_3$ and $R_4$ are each are hydrogen or lower alkyl.

* * * * *